United States Patent [19]

Kunzler et al.

[11] Patent Number: 5,710,302
[45] Date of Patent: Jan. 20, 1998

[54] MONOMERIC UNITS USEFUL FOR REDUCING THE MODULES OF SILICONE HYDROGELS

[75] Inventors: Jay F. Kunzler, Canandaigua; Richard M. Ozark, Solvay, both of N.Y.

[73] Assignee: Bausch & Lomb Incorporated, Rochester, N.Y.

[21] Appl. No.: 745,538

[22] Filed: Nov. 12, 1996

[51] Int. Cl.$^6$ ........................... C07F 7/04
[52] U.S. Cl. ........................... 556/434; 526/279
[58] Field of Search ............ 556/434; 526/279

[56] References Cited

U.S. PATENT DOCUMENTS

| | | | |
|---|---|---|---|
| 4,153,641 | 5/1979 | Deichert et al. | 260/827 |
| 4,189,546 | 2/1980 | Deichert et al. | 528/26 |
| 4,259,467 | 3/1981 | Keogh et al. | 526/279 |
| 4,709,066 | 11/1987 | Chapman . | |
| 4,727,172 | 2/1988 | Yamamoto et al. . | |
| 4,740,533 | 4/1988 | Su et al. | 523/106 |
| 4,810,764 | 3/1989 | Friends et al. | 526/245 |
| 4,824,922 | 4/1989 | Chapman . | |
| 4,910,277 | 3/1990 | Bambury et al. | 526/260 |
| 4,954,587 | 9/1990 | Mueller | 526/245 |
| 5,010,141 | 4/1991 | Mueller | 525/276 |
| 5,034,461 | 7/1991 | Lai et al. | 525/100 |
| 5,070,215 | 12/1991 | Bambury et al. | 556/418 |
| 5,079,319 | 1/1992 | Mueller | 526/238.23 |
| 5,142,009 | 8/1992 | Kawaguchi . | |
| 5,250,583 | 10/1993 | Kawaguchi et al. . | |
| 5,260,000 | 11/1993 | Nandu et al. | 264/2.1 |
| 5,310,779 | 5/1994 | Lai | 524/588 |
| 5,321,108 | 6/1994 | Kunzler et al. | 526/242 |
| 5,358,995 | 10/1994 | Lai et al. | 524/547 |
| 5,387,662 | 2/1995 | Kunzler et al. | 526/245 |
| 5,391,589 | 2/1995 | Kiguchi et al. . | |
| 5,391,591 | 2/1995 | Kawaguchi et al. . | |
| 5,539,016 | 7/1996 | Kunzler et al. . | |

FOREIGN PATENT DOCUMENTS

| | | |
|---|---|---|
| 62-38419 | 2/1987 | Japan . |
| 4-168115 | 6/1992 | Japan . |

OTHER PUBLICATIONS

"The Role of Bulky Polysiloxanylalkyl Methacrylates in Polyurethane–Polysiloxane Hydrogels" by Yu–Chin Lai—*Polymeric Materials Science and Engineering*, vol. 72, pp. 118–119.

Document No. 107:28430—Kubota et al JP85–178115–850813 In House Computer Operated Abstract pp. 79–83 (19 of 21).

Document No. 107; 28429—Kubota et al JP85–178114850813—In House Computer Operated Abstract p. 83 (Answer 20 of 21).

Document No. 105:173972—Kubota et al JP84–197462–840920—In House Abstract pp. 85–88 (Answer 21 of 21).

Document No. 118:87685 Tetsuo et al JP90–292073–901031 In House Abstract pp. 90–91 (Answer 2 of 2).

*Primary Examiner*—Joseph L. Schofer
*Assistant Examiner*—N. Sarofim
*Attorney, Agent, or Firm*—John E. Thomas

[57] ABSTRACT

Monomeric units useful in reducing the modulus of hydrogels are disclosed. Silicone hydrogels including the subject monomeric units are especially useful in the formation of biomedical articles such as silicone hydrogel contact lenses.

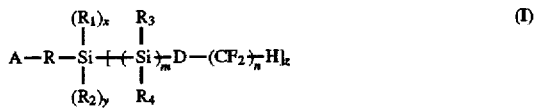

(I)

wherein:
  A is an activated unsaturated group;
  R and D independently are alkyl, alkylene or haloalkyl groups having 1 to 10 carbon atoms wherein said carbon atoms may include ether linkages therebetween;
  $R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;
  m is an integer from 1 to 500; n is an integer from 1 to 20;
  x and y are 0 or 1;
  z is 1 or 2; and x+y+z=3;
  so long as at least one of $R_1$ or $R_2$ is an alkyl group having from 1 to 10 carbon atoms.

13 Claims, No Drawings

MONOMERIC UNITS USEFUL FOR REDUCING THE MODULES OF SILICONE HYDROGELS

PRIOR APPLICATIONS

This application claims the benefit of U. S. Provisional Application No. 60/008,297 filed on Dec. 7, 1995.

FIELD OF THE INVENTION

The present invention relates to a class of fluorinated siloxane-containing monomeric units and their use in reducing the modulus of silicone hydrogels. Such materials find particular application in the formation of contact lenses.

BACKGROUND

Hydrogels represent a desirable class of materials for many biomedical applications, including the formation of contact lenses. Hydrogels are hydrated, cross-linked polymeric system that contain water in an equilibrium state. Silicone hydrogels are a well known class of hydrogel and are characterized by the inclusion of silicone. Silicone hydrogels generally have a water content greater than about 5 weight percent and more commonly between about 10 to about 80 weight percent. Such materials are usually prepared by polymerizing a mixture containing at least one silicone-containing monomer and at least one hydrophilic monomer. Either the silicone-containing monomer or the hydrophilic monomer may function as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of applicable silicone-containing monomeric units include:

(a) bulky polysiloxanylalkyl (meth)acrylic monomers, commonly referred to as "TRIS" monomers, including for example: methacryloxypropyl tris(trimethylsiloxy) silane;

(b) poly(organosiloxane) monomeric units;

(c) silicone containing monomers includes silicone-containing vinyl carbonate or vinyl carbamate monomers such as; 1,3-bis[4-vinyloxycarbonyloxy)but-1-yl] tetramethyldisiloxane; 3-(trimethylsilyl)propyl vinyl carbonate; 3-(vinyloxycarbonylthio)propyl-[tris (trimethylsiloxy)silane]; 3-[tris(trimethylsiloxy)silyl] propyl vinyl carbamate; 3-[tris(trimethylsiloxy)silyl] propyl allyl carbamate; 3-[tris(trimethylsiloxy)silyl] propyl vinyl carbonate; t-butyldimethylsiloxyethyl vinyl carbonate; trimethylsilylethyl vinyl carbonate; trimethylsilylmethyl vinyl carbonate. Other examples of applicable silicone-containing monomers are well known in the art.

Silicone-containing monomers may be copolymerized with a wide variety of hydrophilic monomers to produce a variety of silicone hydrogel products. For example, silicone hydrogels are particularly useful in a variety of biomedical applications including the formation of shaped articles and coatings such as; membranes, films, artificial ureters, diaphragms, intrauterine devices, heart valves, vessel substitutes, surgical devices, catheters, mouth guards, denture liners, intraocular devices, prosthetic devices, and especially contact lenses.

Suitable hydrophilic monomers for use in silicone hydrogels include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone; and acrylamides, such as methacrylamide and N,N-dimethylacrylamide. Still further examples are the hydrophilic vinyl carbonate or vinyl carbamate monomers disclosed in U.S. Pat. Nos. 5,070,215, and the hydrophilic oxazolone monomers disclosed in U.S. Pat. No. 4,910,277. Other suitable hydrophilic monomers will be apparent to one skilled in the art.

In particular regard to contact lenses, the fluorination of certain monomers used in the formation of silicone hydrogels has been indicated to reduce the accumulation of deposits on contact lenses made therefrom, as described in U.S. Pat. Nos. 4,954,587, 5,079,319 and 5,010,141. Moreover, the use of silicone-containing monomers having certain fluorinated side groups, i.e. —($CF_2$)—H, have been found to improve compatibility between the hydrophilic and silicone-containing monomeric units, as described in U.S. Pat. Nos. 5,387,662 and 5,321,108.

Many silicone hydrogels possess relatively high moduli (Young's modulus of elasticity), e.g. often in excess of 300 g/mm$^2$ as measured by ASTM test method D1938. For many biomedical applications, it is desirable to provide hydrogels having reduced moduli, e.g. in the range of about 20 g/mm$^2$ to about 150 g/mm$^2$, and more preferably from about 30 g/mm$^2$ to about 100 g/mm:. This is particularly important in the formation of soft contact lenses, as the modulus of lens material can have a significant impact upon lens "comfort." Lenses possessing high moduli often have a perceived stiffness and undesirably high elastic recovery resulting in an unnatural feeling when worn upon the eye.

The use of bulky polysiloxanylalkyl methacrylates, e.g. methacryloxypropyl tris (trimethylsiloxy) silane, referred to above as "TRIS", are known to reduce the modulus of one class of silicone hydrogels, i.e. polyurethane-polysiloxane hydrogel compositions. See for example; Lai, Yu Chin, *The Role of Bulky Polysiloxanylalkyl Methacrylates in Polyurethane-polysiloxane Hydrogels*, Proceedings of the American Chemical Society Division of Polymeric Materials: Science and Engineering, Vol 72, pg. 118–119, (1995). The use of TRIS compounds in silicone hydrogels is also described in U.S. Pat. No. 5,358,995. In U.S. Pat. Nos. 5,321,108 and 5,387,662, a TRIS-type compound is disclosed which includes at least one fluoro substituted end group including a terminal hydrogen. Such materials are described as providing increase compatibility as between silicone-containing and hydrophilic monomeric units.

Unfortunately, the aforementioned TRIS-type fluorinated compounds have relatively high boiling points, and as such, are not distillable through conventional techniques. As a consequence, purification of such materials can be difficult. For this same reason, these materials can also be difficult to analyze, e.g. by way of gas chromatography.

Thus, silicone hydrogels are sought which maintain acceptable oxygen permeability while possessing reduced moduli and which are more easily synthesized, purified, and analyzed. Furthermore, in many applications, such hydrogels must be optically clear, manufacturable (e.g., capable of being molded, machined, etc.) into such products as contact lenses, biocompatible, and less prone to deposit formation.

SUMMARY OF THE INVENTION

The present invention is a monomeric unit useful for reducing the modulus of silicone hydrogels and is represented by Formula I:

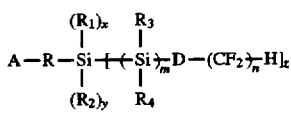

(I)

wherein:

A is an activated unsaturated group;

R and D independently are alkyl, alkylene or haloalkyl groups having 1 to 10 carbon atoms wherein said carbon atoms may include ether linkages therebetween;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20; x and y are 0 or 1;

z is 1 or 2; and x+y+z=3;

so long as at least one of $R_1$ or $R_2$ is an alkyl group having from 1 to 10 carbon atoms.

The present invention further includes hydrogel compositions including the subject monomeric unit, methods for reducing the moduli of hydrogels, methods for making hydrogels, and contact lenses made from such hydrogels.

An advantage of the subject invention is that the monomer units described with reference to Formula I reduce the modulus of hydrogels without significantly reducing the oxygen permeability of the resulting polymeric composition. Furthermore, the subject monomeric units are relatively easy to synthesize, purify, and analyze, and may be polymerized within the hydrogel without significantly effecting optical clarity.

DETAILED DESCRIPTION OF THE INVENTION

The present invention relates to monomeric units represented by Formula I (described below), and the use of such monomeric units to reduce the modulus of silicone hydrogels. Silicone hydrogels of the present invention are typically formed by polymerizing a monomer mix comprising from about 10 to about 89 weight percent but preferably about 25 to about 50 weight percent of silicone-containing monomeric units, from about 10 to about 70 weight percent but preferably from about 20 to about 60 weight percent of hydrophilic monomeric units, and from about 1 to about 50 weight percent but preferably from about 5 to about 20 weight percent of monomeric units represented by Formula I:

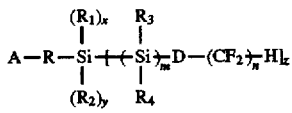

(I)

wherein:

A is an activated unsaturated group;

R and D independently are an alkyl, alkylene or haloalkyl group having 1 to 10 carbon atoms wherein said carbon atoms may include ether linkages therebetween;

$R_1$, $R_2$, $R_3$ and $R_4$ are independently selected from: alkyl or haloalkyl groups, (including both unsubstituted alkyl groups e.g. groups having from 1 to 18 carbon atoms, and substituted alkyl groups e.g. halogen substituted alkyl and hydroxy substituted alkyl), wherein ether linkages may be included between carbon atoms; siloxane groups; and carbocyclic ring groups having from 6 to 18 carbon atoms. e.g. cyclohexyl or phenyl groups which may include alkyl side groups;

m is an integer equal to 1 or greater but is preferably less than 500, and more preferably from 1 to about 10, and still more preferably from 1 to 3;

n is an integer from 1 to 20 but is preferably from 1 to 6;

x and y are 0 or 1;

z is 1 or 2; and x+y+z=3;

so long as at least one of $R_1$ or $R_2$ is an alkyl group having from 1 to 10 carbon atoms.

Monomeric units of type represented by Formula I can be synthesized by techniques well known in the art. Specific methodologies for making preferred monomeric units are provided within the Example section below.

In some preferred embodiments, z is 1, and $R_1$ through $R_4$ are independently selected from alkyl groups, e.g. lower alkyl groups such as those having from 1 to 10 carbon atoms, e.g. methyl, ethyl, propyl, etc., and fluoro-substituted lower alkyl groups. A specific example of a preferred monomeric unit includes that represented by Formula II:

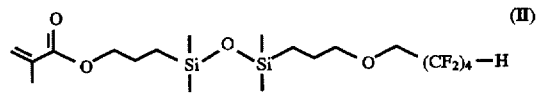

(II)

Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995. Specific examples of applicable silicone-containing monomeric units include ethylenically "end-capped" siloxane-containing monomeric units used in the subject composition may be represented by Formula III:

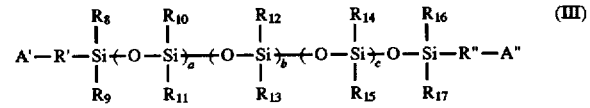

(III)

wherein:

A' and A" are activated unsaturated groups;

R' and R" independently are an alkyl or alkylene group having 1 to 10 carbon atoms wherein the carbon atoms may include ether linkages therebetween;

$R_8$ through $R_7$ are independently selected from monovalent hydrocarbon radicals or halogen substituted monovalent hydrocarbon radicals having 1 to 18 carbon atoms which may include ether linkages therebetween, but preferably are chosen from the groups described with reference to $R_1$ though $R_4$;

a is an integer equal to or greater than 1;

b and c are integers equal to or greater than 0; and a+b+c equals an integer from 1 to 1000.

Preferably, $R_8$ through $R_{17}$ are independently selected from alkyl groups, including both unsubstituted alkyl groups and substituted alkyl groups such as fluoro-substituted alkyl groups. It is further preferred that at least one of $R_8$ through $R_{17}$ includes a fluoro-substituted alkyl group such as that represented by the formula:

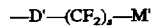

wherein:

D' is an alkyl or alkylene group having 1 to 10 carbon atoms wherein said carbon atoms may include ether linkages therebetween;

M' is hydrogen, fluorine, or alkyl group (e.g. an alkyl group having from 1 to 10 carbon atoms) but preferably hydrogen or fluorine; and s is an integer from 1 to 20, preferably 1 to 6.

With respect to A, A', and A", the term "activated" is used to describe unsaturated groups which include at least one substituent which facilitates free radical polymerization. Preferably the activating groups facilitate polymerization under mild conditions, such as ambient temperatures. Although a wide variety of such groups may be used, preferably, A, A', and A" are esters or amides of an acrylic or methacrylic acid represented by the general formula:

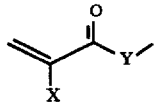

wherein X is preferably hydrogen or methyl but may include other groups, e.g cyano, and Y represents —O—, —S—, or 13 NH—, but is preferably —O—. Examples of other suitable groups include vinyl carbonates, vinyl carbamates, acrylonitryl, and styryl. Still another example of a suitable group includes N-vinyl-2-pyrrolidinone-(3, 4, or 5)yl as shown in the following formula:

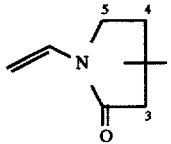

D, R, R', and R" represent divalent hydrocarbon radicals, preferably alkyl or alkylene groups having 1 to 10 and which may include ether linkages between carbon atoms. Preferably such alkyl or alkylene groups include 1 to 6 carbon atoms. Examples of such groups include methylene, propylene, butylene, pentamethylene, hexamethylene, etc., arylene radicals such as phenylene and biphenylene, and —O—$(CH_2)_q$—, wherein q is preferably 1 to 6.

Specific examples of preferred monomeric units include those represented by Formulae IV and V:

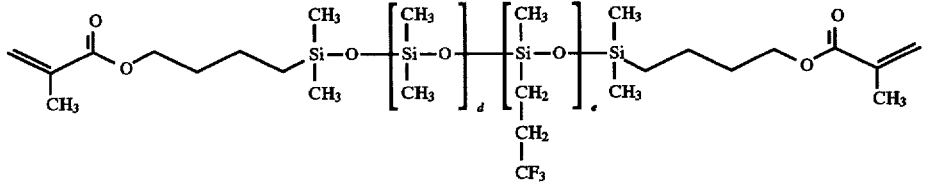

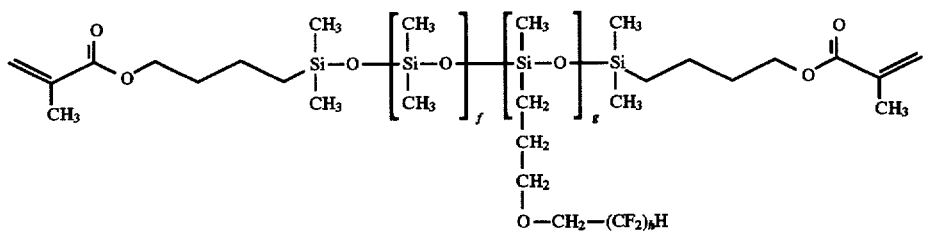

wherein:

d, e, f, and g, are integers from 0 to 1000, d+e equals an integer from 2 to 1000, preferably 2 to 100, f+g equals an integer from 2 to 1000, preferably 2 to 100, wherein e and g are preferably integers from about 20 to about 50, and h is an integer from 1 to about 20.

The synthesis of monomeric units as represented by Formula III, IV, are V are well known in the art. Specific examples are provided in the Example section below.

Further examples of suitable silicone-containing monomers include bulky polysiloxanylalkyl (meth)acrylic monomers represented by Formula VI:

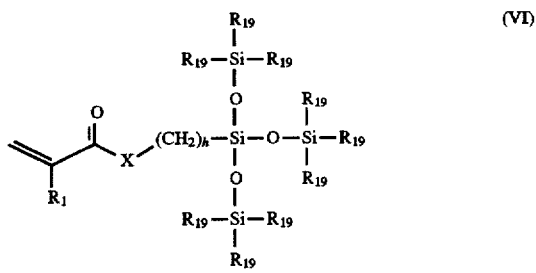

wherein:

X denotes —O— or —NR—;

each $R_{18}$ independently denotes hydrogen or methyl;

each $R_{19}$ independently denotes a lower alkyl radical or a phenyl radical; and h is 1 to 10.

Such bulky monomers include methacryloxypropyl tris (trimethylsiloxy)silane.

Another preferred class of silicone containing monomers includes silicone-containing vinyl carbonate or vinyl carbamate monomers of Formula VII:

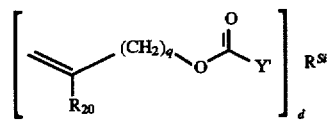

wherein:

Y' denotes —O—, —S— or —NH—;

$R^{Si}$ denotes a silicone-containing organic radical;

$R_{20}$ denotes hydrogen or methyl;

d is 1, 2, 3 or 4; and q is 0 or 1.

Suitable silicone-containing organic radicals $R^{Si}$ include the following:

—$(CH_2)_n$-Si[$(CH_2)_m$CH$_3$]$_3$;

—$(CH_2)_n$-Si[OSi$(CH_2)_m$CH$_3$]$_3$;

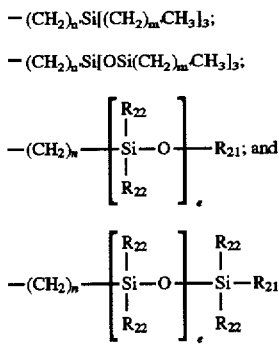

wherein:

$R_{21}$ denotes

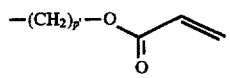

wherein p' is 1 to 6;

$R_{22}$ denotes an alkyl radical or a fluoroalkyl radical having 1 to 6 carbon atoms;

e is 1 to 200;

n' is 1, 2, 3 or 4; and m' is 0, 1, 2, 3, 4 or 5.

The silicone-containing vinyl carbonate or vinyl carbamate monomers specifically include: 1,3-bis[4-vinyloxycarbonyloxy)but-1-yl]tetramethyl-disiloxane; 3-(trimethyl silyl) propyl vinyl carbonate; 3-(vinyloxycarbonylthio)propyl-[tris(trimethylsiloxy) silane]; 3-[tris (trimethylsiloxy)silyl] propyl vinyl carbamate; 3-[tris(trimethylsiloxy)silyl] propyl allyl carbamate; 3-[tris(trimethylsiloxy)silyl] propyl vinyl carbonate; t-butyldimethylsiloxyethyl vinyl carbonate; trimethylsilylethyl vinyl carbonate; trimethylsilylmethyl vinyl carbonate; and "V$_2$D$_{25}$", represented by Formula VIII.

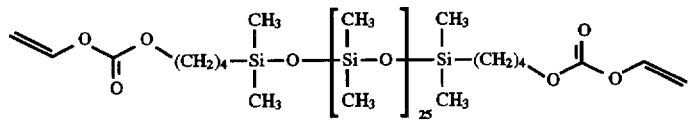

A further preferred class of silicone-containing monomers includes monomers of the Formulae IX and X:

wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A denotes a divalent polymeric radical of Formula XI:

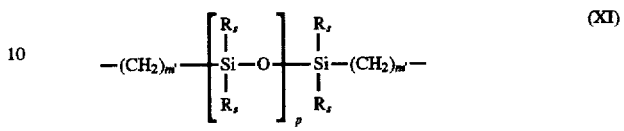

wherein:

each Rs independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula XII:

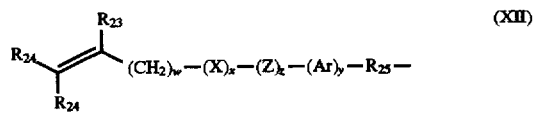

wherein:

$R_{23}$ is hydrogen or methyl;

$R_{24}$ is hydrogen, an alkyl radical having 1 to 6 carbon atoms, or a —CO—Y—$R_{26}$ radical wherein Y is —O—, —S— or —NH—;

$R_{25}$ is a divalent alkylene radical having 1 to 10 carbon atoms;

$R_{26}$ is a alkyl radical having 1 to 12 carbon atoms;

X denotes —CO— or —OCO—;

Z denotes —O— or —NH—;

Ar denotes an aromatic radical having 6 to 30 carbon atoms;

w is 0 to 6;

x is 0 or 1;

y is 0 or 1; and z is 0 or 1.

A preferred urethane monomer is represented by Formula (XIII):

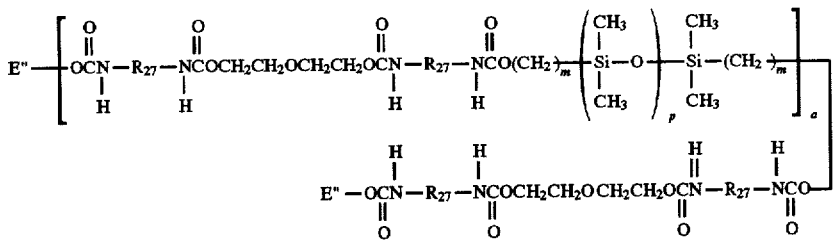

wherein m is at least 1 and is preferably 3 or 4, a is at least 1 and preferably is 1, p is a number which provides a moiety weight of 400 to 10,000 and is preferably at least 30, $R_{27}$ is a diradical of a diisocyanate after removal of the isocyanate group, such as the diradical of isophorone diisocyanate, and each E" is a group represented by:

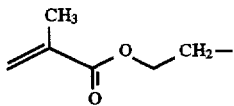

The monomer mix of the present invention may include additional constituents such as crosslinking agents, internal wetting agents, hydrophilic monomeric units, toughening agents, and other constituents as is well known in the art.

Although the some of the previously described silicone-containing monomeric units form a crosslinked three-dimensional network when polymerized, additional crosslinking agents may be added to the monomer mix. Examples of suitable crosslinking agents include: polyvinyl, typically di- or tri-vinyl monomers, most commonly the di- or tri(meth)acrylates of dihydric ethylene glycol, triethylene glycol, butylene glycol, hexane 1,6-diol, thio-diethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM) as disclosed in U.S. Pat. No. 4,954,587.

Other known crosslinking agents are polyether-bisurethane-dimethacrylates as described in U.S. Pat. No. 4,192,827, and those crosslinkers obtained by reaction of polyethylene glycol, polypropylene glycol and polytetramethylene glycol with 2-isocyanatoethyl methacrylate (IEM) or m-isopropenyl-γ,γ,-dimethylbenzyl isocyanates (m-TMI), and polysiloxane-bisurethane-dimethacrylates as described in U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

Although not required, compositions within the scope of the present invention may include toughening agents, preferably in quantities of less than about 80 weight percent e.g. from about 5 to about 80 weight percent, and more typically from about 20 to about 60 weight percent. Examples of suitable toughening agents are described in U.S. Pat. No. 4,327,203. These agents include cycloalkyl acrylates or methacrylates, such as: methyl acrylate and methacrylate, tertiarybutylcyclohexyl methacrylate, isopropylcyclopentyl acrylate, tertiarypentylcyclo-heptyl methacrylate, tertiary-butylcyclohexyl acrylate, isohexylcyclopentyl acrylate and methylisopentyl cyclooctyl acrylate. Additional examples of suitable toughening agents are described in U.S. Pat. No. 4,355,147. This reference describes polycyclic acrylates or methacrylates such as: isobornyl acrylate and methacrylate, dicyclopentadienyl acrylate and methacrylate, adamantyl acrylate and methacrylate, and isopinocamphyl acrylate and methacrylate. Further examples of toughening agents are provided in U.S. Pat. No. 5,270,418. This reference describes branched alkyl hydroxyl cycloalkyl acrylates, methacrylates, acrylamides and methacrylamides. Representative examples include: 4-t-butyl, 2-hydroxycyclohexyl methacrylate (TBE);: 4-t-butyl, 2-hydroxycyclopentyl methacrylate; methacryloxyamino-4-t-butyl-2-hydroxycyclohexane; 6-isopentyl, 3-hydroxycyclohexyl methacrylate; and methacryloxyamino, 2-isohexyl, 5-hydroxycyclopentane.

Internal wetting agents may also be used for increasing the wettability of such hydrogel compositions. Examples of suitable internal wetting agents include N-alkyenoyl trialkylsilyl aminates as described in U.S. Pat. No. 4,652,622. These agents can be represented by the general formula:

wherein:
E is hydrogen or methyl,
G is $(CH_2)_rC(O)OSi(V)_3$ or hydrogen,
V is methyl, ethyl or propyl,
q is an integer form 1 to 15,
r is an integer form 1 to 10,
q+r is an integer form 1 to 15, hereinafter referred to as NATA.

Acryloxy- and methacryloxy-, mono- and dicarboxylic amino acids, hereinafter NAA, impart desirable surface wetting characteristics to polysiloxane polymers, but precipitate out of siloxane monomer mixtures before polymerization is completed. NAA can be modified to form trialkylsilyl esters which are more readily incorporated into polysiloxane polymers. The preferred NATAs are trimethylsilyl-N-methacryloxyglutamate, triethylsilyl-N-methacryloxyglutamate, trimethyl-N-methacryloxy-6-aminohexanoate, trimethylsilyl-N-methacryloxy-aminododecanoate, and bis-trimethyl-silyl-N-methacryloxy aspartate.

Preferred wetting agents also include acrylic and methacylic acids, and derivatives thereof. Typically, such wetting agents comprise less than 5 weight percent of the composition.

Other preferred internal wetting agents include oxazolones as described in U.S. Pat. No. 4,810,764 to Friends et al.

issued Mar. 7, 1989. These materials can be represented by the formula:

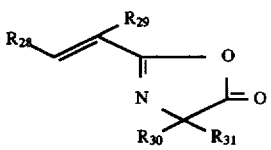

wherein:

$R_{28}$ and $R_{29}$ are independently selected from hydrogen or methyl, and $R_{30}$ and $R_{31}$ are independently selected from methyl of cyclohexyl radicals.

These preferred internal wetting agents specifically include 2-isopropenyl-4,4-dimethyl-2-oxazolin-5-one (IPDMO), 2-vinyl-4,4-dimethyl-2-oxazolin-5-one (VDMO), cyclohexane spiro-4'-(2'isopropenyl-2'-oxazol-5'-one) (IPCO), cyclohexane-spiro-4'-(2'-vinyl-2'-oxazol-5'-one) (VCO), and 2-(-1-propenyl)-4,4-dimethyl-oxazol-5-one (PDMO). The preparation of such oxazolones is known in the art and is described in U.S. Pat. No. 4,810,764.

These preferred internal wetting agents have two important features which make them particularly desirable wetting agents: (1) they are relatively non-polar and are compatible with the hydrophobic monomers (the polysiloxanes and the toughening agents), and (2)they are converted to highly polar amino acids on mild hydrolysis, which impart substantial wetting characteristics. When polymerized in the presence of the other components, a copolymer is formed. These internal wetting agents polymerize through the carbon-carbon double bond with the endcaps of the polysiloxane monomers, and with the toughening agents to form copolymeric materials particularly useful in biomedical devices, especially contact lenses.

As indicated, the subject hydrogel compositions includes hydrophilic monomeric units. Examples of appropriate hydrophilic monomeric units include those described in U.S. Pat. Nos.: 4,259,467; 4,260,725; 4,440,918; 4,910,277; 4,954,587; 4,990,582; 5,010,141; 5,079,319; 5,310,779; 5,321,108; 5,358,995; 5,387,662; all of which are incorporated herein by reference. Examples of preferred hydrophilic monomers include both acrylic- and vinyl-containing monomers.

Preferred hydrophilic monomers may be either acrylic- or vinyl-containing. Such hydrophilic monomers may themselves be used as crosslinking agents. The term "vinyl-type" or "vinyl-containing" monomers refers to monomers containing the vinyl grouping ($CH_2=CQH$), and are generally highly reactive. Such hydrophilic vinyl-containing monomers are known to polymerize relatively easily. "Acrylic-type" or "acrylic-containing" monomers are those monomers containing the acrylic group represented by the formula:

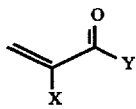

wherein X is preferably hydrogen or methyl and Y is preferably —O—, —OQ—, —NH—, —NQ— and —NH (Q)—, wherein Q is typically an alkyl or substituted alkyl group. Such monomers are known to polymerize readily.

Preferred hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, with NVP being the most preferred.

Preferred hydrophilic acrylic-containing monomers which may be incorporated into the hydrogel of the present invention-include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred.

When both an acrylic-containing monomer and a vinyl-containing monomer are incorporated into the invention, a further crosslinking agent having both a vinyl and an acrylic polymerizable group may be used, such as the crosslinkers which are the subject of U.S. Pat. No. 5,310,779, issued May 10, 1994, the entire content of which is incorporated by reference herein. Such crosslinkers help to render the resulting copolymer totally UV-curable. However, the copolymer could also be cured solely by heating, or with a combined UV and heat regimen. Photo and/or thermal initiators required to cure the copolymer will be included in the monomer mix, as is well-known to those skilled in the art. Other crosslinking agents which may be incorporated into the silicone-containing hydrogel including those previously described.

Other techniques for increasing the wettability of compositions may also be used with the scope of the present invention, e.g. plasma surface treatment techniques which are well known in the art.

Particularly preferred hydrogel compositions comprise from about 5 to about 20 weight percent of monomeric units represented by Formula I, from 5 to 60 weight percent of the monomeric units represented by Formula IV, and from 20 to 60 weight percent of hydrophilic monomeric units.

The monomer mixes employed in this invention, can be readily cured to cast shapes by conventional methods such as UV polymerization, or thermal polymerization, or combinations thereof, as commonly used in polymerizing ethylenically unsaturated compounds. Representative free radical thermal polymerization initiators are organic peroxides, such as acetal peroxide, lauroyl peroxide, decanoyl peroxide, stearoyl peroxide, benzoyl peroxide, tertiarybutyl peroxypivalate, peroxydicarbonate, and the like, employed in a concentration of about 0.01 to 1 percent by weight of the total monomer mixture. Representative UV initiators are those known in the field such as, benzoin methyl ether, benzoin ethyl ether, Darocur 1173, 1164, 2273, 1116, 2959, 3331 (EM Industries) and Igracur 651 and 184 (Ciba-Geigy). Polymerization of the monomeric units of this invention with other comonomers is generally performed (with crosslinking agents) in the presence of a diluent. The polymerization product will then be in the form of a gel. If the diluent is nonaqueous, the diluent must be removed from the gel and replaced with water through the use of extraction and hydration protocols well known to those skilled in the art. It is also possible to perform the polymerization in the absence of diluent to produce a xerogel. These xerogels may then be hydrated to form the hydrogels as is well known in the art.

In addition to the above-mentioned polymerization initiators, the copolymer of the present invention may also include other monomers as will be apparent to one skilled in the art. For example, the monomer mix may include colorants, or UV-absorbing agents such as those known in the contact lens art.

The present invention provides materials which can be usefully employed for the fabrication of prostheses such as heart valves and intraocular lenses, films, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices, and especially contact lenses.

The polymers of this invention can be formed into contact lenses by spincasting processes (such as those disclosed in U.S. Pat. Nos. 3,408,429 and 3,496,254), cast molding, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

When used in the formation of contact lenses, it is preferred that the subject hydrogels have water contents of from about 20 to about 70 weight percent. Furthermore, it is preferred that such hydrogels have a modulus from about 20 g/mm² to about 150 g/mm², and more preferably from about 30 g/mm² to about 100 g/mm².

As an illustration of the present invention, several examples are provided below. These examples serve only to further illustrate aspects of the invention and should not be construed as limiting the invention.

EXAMPLE I

Several hydrogel polysiloxane compositions were prepared including varying ratios of the ethylenically terminated siloxane-containing monomeric units represented by Formula V (RD542), hydrophilic monomeric units, N,N-dimethylacrylamide (DMA), and the subject monomeric unit represented by Formula II, (MO). The specific ratio of each monomeric units is provided in Table I below. The example compositions were tested for various mechanical properties, the results of which are also reported in Table I.

The monomeric unit generally represented by Formula V, i.e. poly (25 mole % octafluoropentyloxypropylmethylsiloxane)-co-(75 mole % dimethylsiloxane), referred to as "RD542" below, was prepared as follows.

(a) Preparation of a DP 100 methacrylate end-capped poly 75 mole % dimethyl siloxane-co-25 mole % methyl siloxane hydride prepolymer To a 1000 ml round bottom flask under dry nitrogen is added octamethylcyclotetrasiloxane (371.9 g, 1.25 mole), tetramethylcyclotetrasiloxane (100.4 g, 0.42 mole) and 1,3-bis-methacryloxybutyltetramethyldisiloxane (27.7 g 0.7 mole). Trifluoromethane sulfonic acid (0.25%, 1.25 g) is added as initiator. The reaction mixture is stirred overnight at room temperature. Ten grams of sodium bicarbonate is then added and the reaction mixture is again stirred overnight. The resultant solution is filtered and placed under high vacuum at 50° C. to remove the unreacted cyclic compounds. The prepolymer structure is confirmed by NMR spectroscopy.

(b) Preparation of a DP 100 methacrylate end-capped poly 75 mole % dimethyl siloxane-co-25 mole % (methyl octafluoropentyloxypropyl) siloxane prepolymer To a 500 ml round bottom flask equipped with a magnetic stirrer and water condenser, is added 15 g (0.002 mole) of the silicone hydride prepolymer (prepared above), 27.2 g (0.1mole) of allyloxyoctafluoropentane, 60 gl of a tetramethyldisiloxane platinum complex (available from Huels) and 80 mls of anhydrous tetrahydrofuran and 80 mls of dioxane under dry nitrogen. The reaction mixture is heated to 75° C. and the reaction is monitored by IR spectroscopy for loss of silicone hydride. When the silicone hydride has reacted, the reaction mixture is cooled and the unreacted allyoxyoctafluoropentane is removed by heating the product under high vacuum at 50° C. for one hour. The structure of the resultant octafluoro substituted prepolymer is confirmed by NMR spectroscopy.

The monomeric unit represented by Formula II, i.e. 1-(methacryloxypropyl)-3-(3-(2,2,3,3,4,4,5,5-octafluoropentoxy)-propyl) tetramethyldisiloxane, referred to as "MO" below, was prepared as follows:

(a) Preparation of trimethylsilyl protected hydroxypropyl tetramethyldisiloxane

To a 1 L round bottom flask is added 1,3-tetramethyldisiloxane (100 g, 0.774 mole), allyloxytrimethylsilane (97.0 g, 0.779 mole), 0.008 g of a (TRIS (triphenylphosphine) rhodium) chloride and 400mls of toluene. The solution is heated to 80° C. for two hours at which time the silicone hydride is reacted as shown by ¹H-NMR spectroscopy. The toluene is removed using a rotoevaporator and the resultant oil is vacuum distilled (65° C./1.5 mmHg) to yield 127.5 g (64.8% yield) of trimethylsilyl protected hydroxy propyl tetramethyldisiloxane.

(b) Preparation of 1 -(3-trimethylsilyloxypropyl)-3-(3-(2,2,3,3,4,4,5,5-octafluoropentoxy)-propyl) tetramethyldisiloxane To a 1 L round bottom flask is added trimethylsilyl protected hydroxy propyl tetramethyldisiloxane (60 g, 0.227 mole), allyloxyoctafluoropentane (74.1 g, 0.272 mole), platinum divinyl tetramethyldisiloxane complex (113 ul, 0.002 mole/ul catalyst), 200 mls of THF and 200 mls of 1,4-dioxane. The solution is heated to 80° C. for three hours at which time the solvent is removed using a rotoevaporator. The resultant oil is passed through 50 g of silica gel using a 10/1 mixture of pentane and methylene chloride. The solvent is removed using a rotoevaporator and the resultant oil is vacuum distilled (120° C./0.2 mmHg) to yield 103 grams of a 97% pure 1-(3-trimethylsilyloxypropyl)-3-(3-(2,2,3,3,4,4,5,5-octafluoro-pentoxypropyl) tetramethyldisiloxane.

(c) 1-(methacryloxypropyl)-3-(3-(2,2,3,3,4,4,5,5-octafluoropentoxy)-propyl) tetra-methyldisiloxane 1-(3-trimethylsilyloxypropyl)-3-(3-(2,2,3,3,4,4,5,5-octafluoro-pentoxy propyl) tetramethyldisiloxane (53.7 g, 0.1 mole) is dissolved in 540 ml of methanol. To this solution is added 8.8 ml of a 10% solution of acetic acid at room temperature. The mixture is stirred for one hour and the solvent is removed on a rotoevaporator at 40° C. The resultant oil is dissolved in 300 mls of hexane and washed four times with distilled water. The organic layer is collected, dried over magnesium sulfate and filtered.

The filtered reaction product from above, (1-(3-hydroxypropyl)-3-(3-(2,2,3,3,4,4,5,5-octafluoropentoxypropyl)-tetramethyldisiloxane), (46.3 g, 0.1 mole), is added to a 1 L round bottom flask along with triethylamine (11.1 g, 0.110 mole). The solution is cooled to 0° C. and methacryloxy chloride (11.1 g, 0.110 mole) is slowly added. Following the addition of methacryloxy chloride, the solution is brought to room temperature and allowed to stir overnight. The next day the resultant solution is extracted two times with 1N HCl, two times with 2N NaOH and two times with distilled water. The organic layer is collected and dried over magnesium sulfate. The solution is filtered and the solvent is removed using a rotoevaporator. The resultant oil is passed through 50 g of silica gel using a 10/1 mixture of pentane and methylene chloride. The solvent is removed using a rotoevaporator and the resultant oil is vacuum distilled (120° C./0.1 mmHg) to yield 34.1 grams (64% yield) of a 95% pure 1-(3-methacryloxypropyl)-3-(3-(2,2,3,3,4,4,5,5-octafluoro-pentoxy propyl) tetramethyldisiloxane.

An overview of this synthesis is represented by the following reaction pathway:

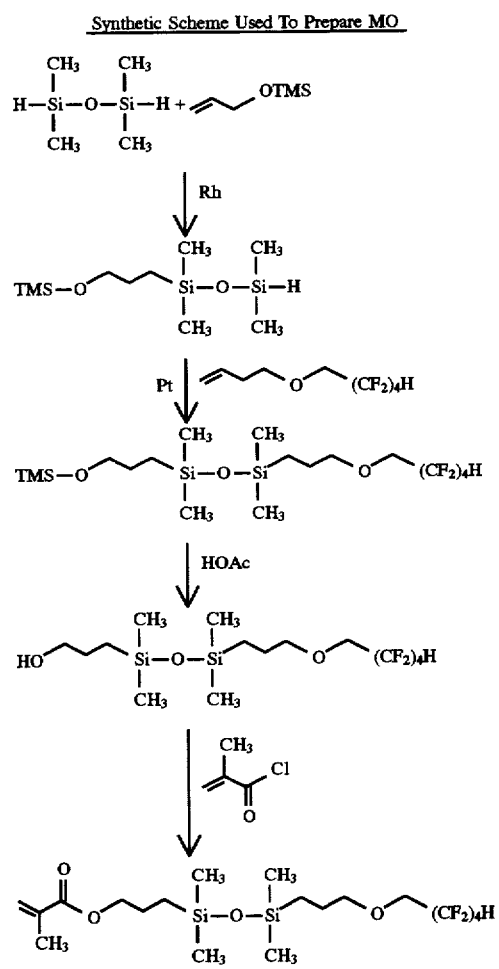

Each of the constituents of each sample were combined in the ratios indicated in Table I, along with a UV initiator, and mixed for approximately 20 minutes. Each of the compositions were individually cast as films and evaluated for several mechanical properties using the following procedure. Films for each composition were cast between silanized glass plates with a 0.3 mm Teflon spacer using cure conditions of 2 hours of UV at an intensity of 3500 μW/cm². The UV initiator was Darocur 1173 (0.5% concentration). The resultant films were extracted 16 hours in 2-propanol and two hours in distilled water followed by a 16 hour hydration in phosphate-buffered saline (pH 7.3). The mechanical properties of films were determined on an Instron Model 4500 using ASTM methods 1708 and 1938. Oxygen permeability (DK) was determined using the polarographic probe method (L. Fatt, J. E. Rasson, and J. B. Melpolder, *ICLC J.*, 14, 38 (1987). The hydrolytic stability test consisted of heating the test films in phosphate-buffered saline for 3, 5, 7, and 14 days at 80° C. and monitoring the change in weight and water content. The results of the mechanical property evaluation for each composition are provided in Table I.

TABLE I

| Composition (Wt. %) RD542/MO/DMA | Young's Modulus (g/mm²) | Tear Strength (g/mm) | Oxygen Permeability (barrers) | Percent Water |
|---|---|---|---|---|
| 70/0/30 | 192 | 3 | 104 | 34 |
| 50/20/30 | 100 | 3 | 70 | 33 |
| 30/40/30 | 29 | 5 | 64 | 34 |

Table I reports the modulus, tear strength, oxygen permeability (DK), and water content for three hydrogel compositions. The first composition was a control and included none of the monomeric unit represented by Formula II. The second and third hydrogel compositions included 20 and 40 weight percent, respectively, of the monomeric unit represented by Formula II, (MO). As is clear from the modulus data of Table I, the control composition had a significantly higher modulus than the other compositions which included MO.

EXAMPLE II

Several hydrogel polysiloxane compositions were prepared, as in Example I, except that the siloxane-containing monomeric units were substituted with a urethane-siloxane-containing monomeric unit, as represented by Formula XIII. More specifically, the urethane monomeric unit is the same as that of Example 11 in U.S. Pat. No. 5,034,461. The preparation of the monomeric unit is known in the art and is also provided U.S. Patent No. 5,034,461. As with Example I, the example compositions were tested for various mechanical properties as reported in Table II.

TABLE II

| Composition (Wt. %) urethane/ MO/DMA | Young's Modulus (g/mm²) | Tear Strength (g/mm) | DK | Tensile (g/mm²) | Elong. % | Percent Water |
|---|---|---|---|---|---|---|
| 70/0/30 | 344 | 3 | 120 | 67 | 29 | 23.4 |
| 60/10/30 | 255 | 3 | 92 | 46 | 25 | 22.8 |
| 50/20/30 | 206 | 3 | 73 | 44 | 31 | 23.9 |
| 40/30/30 | 142 | 4 | 65 | 51 | 60 | 23.3 |

Table II reports the modulus, tear strength, oxygen permeability (DK), elongation, and water content for four hydrogel compositions. The first composition was a control and included none of the monomeric unit represented by Formula II. The second, third, and fourth hydrogel compositions included 10, 20 and 30 weight percent, respectively, of the monomeric unit represented by Formula II, (MO). As is clear from the modulus data of Table II, the control composition had a significantly higher modulus than the other compositions which included MO.

EXAMPLE III

Although the synthesis of monomeric units represented by Formula III are known in the art, an additional representative synthesis is provided for the specific material represented by Formula IV. More specifically, poly (65 mole % trifluoropropylmethylsiloxane)-co-(35 mole % dimethylsiloxane), can be synthesized as follows.

Octamethylcyclotetrasiloxane (39.4 g, 0.133 mole) trifluoropropylcyclotrisiloxane (154.3 g, 0.33 mole) and methacryloxybutyltetramethyldisiloxane (6.3 g, 0.015 mole) were added at room temperature to a round bottom flask under dry nitrogen. Trifluoromethanesulfonic acid (0.54 g, 3.6 mmole) was added and the reaction mixture was stirred for 24 hours. Sodium bicarbonate was then added to the viscous reaction product and the stirring continued for 16 hours. Following the neutralization procedure, chloroform (500mls) was added and the solution was dried over magnesium sulfate and filtered using a 5 µg millipore Teflon filter. The filtrate was placed on a rotary evaporator and the chloroform was removed. The resultant prepolymer was added dropwise with rapid stirring to 500 ml of methanol to remove the unreacted cyclics. The polymer layer was collected and the procedure was repeated twice. Following the third fractionation, the polymer was collected, dissolved in diethylether, dried over magnesium sulfate and again filtered through a 5 µfilter. The resultant solution was placed on the rotary evaporator and the diethylether was removed. The molecular structure of the purified material (150 g, 75%) was confirmed by NMR spectroscopy.

EXAMPLE IV

Although the synthesis of monomeric units represented by Formula I are known in the art, an additional representative synthesis is provided. More specifically, the preparation of Methacrylpropyl di(octafluoropentyloxypropyldimethylsilyl-oxy) methylsilane is provided below.

(a) Preparation of Methacryloxypropyl methyl di(methylsiloxy)silane

To a three neck round bottom flask equipped with a thermometer and magnetic stirrer is added methacryloxypropyldichloromethylsilane (25 g 0.104 mole), dimethylchlorosilane (39.2, 0.415 mole), triethylamine (45.5, 0.450 mole) and 250 ml of anhydrous diethylether. The reaction mixture is cooled to −15° C. and distilled water (14.9, 0.830 mole) is slowly added. The reaction is allowed to come to room temperature slowly and the reaction is stirred overnight. The resultant solution is washed three times with distilled water. The ether layer is collected, dried over magnesium sulfate, filtered and the diethyl ether is removed using a rotoevaporator. The resultant oil is vacuum distilled (105° C./0.15 mm) to give a 50% yield of 94% pure (as determined by GC) methacryloxypropyl tris (dimethysilyloxy) silane.

(b) Preparation of Methacrylpropyl di(octafluoropentyloxypropyldimethylsilyloxy) methylsilane To a 200 ml round bottom flask is added methacryloxypropyl tris (dimethylsilyloxy)silane (8.0 g, 0.0249 mole), allyloxyoctafluoropentane (15 g, 0.055 mole), 0.030 ml of a platinum divinyl complex (huels) and 80 mls of tetrahydrofuran. The solution is refluxed for one hour at which time the silicone hydride is reacted as shown by ¹H-NMR spectroscopy. The THF and unreacted allyloxyoctafluoropentane is removed using a rotoevaporator (50° C./30 mm) resulting in a quantitative yield of methacrylpropyl di(octafluoropentyloxypropyldimethylsilyloxy)methylsilane Many other modifications and variations of the present invention are possible to the skilled practitioner in the field in light of the teachings herein. It is therefore understood that, within the scope of the claims, the present invention can be practiced other than as herein specifically described.

We claim:

1. A monomeric unit represented by Formula I:

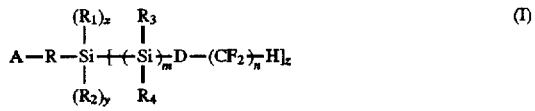

wherein:

A is a polymerizable ethylenically,

R and D independently are alkyl, alkylene or haloalkyl groups having 1 to 10 carbon atoms wherein said carbon atoms may include ether linkages therebetween;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20; x and y are 0 or 1;

z is 1 or 2; and x+y+z=3;

so long as at least one of $R_1$ or $R_2$ is an alkyl group having from 1 to 10 carbon atoms.

2. The monomeric unit of claim 1 wherein z is 1, and $R_1$ and $R_2$ are independently selected from alkyl groups having from 1 to 10 carbon atoms.

3. The monomeric unit of claim 2 wherein at least one of said alkyl groups is fluoro-substituted.

4. The monomeric unit of claim 1 wherein A is a group selected from: an ester or amide of acrylic acid or methacrylic acid.

5. The monomeric unit of claim 1 wherein R and D are alkyl groups having from 1 to 6 carbon atoms wherein said carbon atoms may include ether linkages therebetween.

6. The monomeric unit of claim 1 wherein $R_1$, $R_2$, $R_3$ and $R_4$ are independently selected from alkyl groups having from 1 to 10 carbon atoms.

7. The monomeric unit of claim 1 wherein n is from 1 to 6; and m is from 1 to 10.

8. The monomeric unit of claim 1 represented by Formula II:

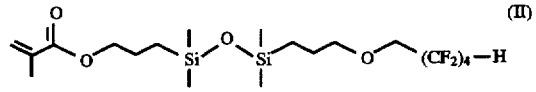

9. A method for making a hydrogel composition including the step of polymerizing a monomer mix comprising monomeric units represented by Formula I:

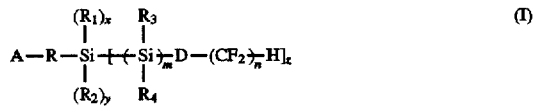

wherein:

A is a polymerizable ethylenically unsaturated radical;

R and D independently are alkyl, alkylene or haloalkyl groups having 1 to 10 carbon atoms wherein said carbon atoms may include ether linkages therebetween;

$R_1$, $R_2$, $R_3$ and $R_4$ are independently selected from: alkyl or haloalkyl groups wherein ether linkages may be included between carbon atoms; siloxane groups; and carbocyclic ring groups having from 6 to 18 carbon atoms;

m is an integer from 1 to 500; n is an integer from 1 to 20; x and y are 0 or 1;

z is 1 or 2; and x+y+z=3;

so long as at least one of $R_1$ or $R_2$ is an alkyl group having from 1 to 10 carbon atoms.

10. The method of claim 9 wherein z is 1; $R_1$, $R_2$, $R_3$, and $R_4$ are independently selected from alkyl groups having from 1 to 10 carbon atoms; A is a group selected from: an ester or amide of acrylic acid or methacrylic acid; R and D are alkyl groups having from 1 to 6 carbon atoms wherein said carbon atoms may include ether linkages therebetween; m is from 1 to 10; and n is from 1 to 6.

11. The method of claim 10 wherein the step of polymerizing a monomer mix is further characterized by preparing a monomer mix comprising:

(a) from about 10 to about 89 weight percent of silicone-containing monomeric units;

(b) from about 10 to about 70 weight percent of hydrophilic monomeric units; and (c) from about 1 to about 50 weight percent of the monomeric units represented by Formula I.

12. The method of claim 11 wherein said silicone-containing monomeric units comprise monomeric units represented by Formula III:

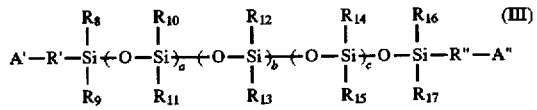

wherein:

A' and A" are activated unsaturated groups;

R' and R" independently are an alkyl or alkylene group having 1 to 10 carbon atoms wherein the carbon atoms may include ether linkages therebetween;

$R_8$ through $R_{17}$ are independently selected from the groups described with reference to $R_1$ though $R_4$;

a is an integer equal to or greater than 1;

b and c are integers equal to or greater than 0; and a+b+c equals an integer from 1 to 1000.

13. The method of claim 12 wherein A' and A" are groups selected from: an ester or amide of acrylic acid or methacrylic acid; R' and R" are selected from are alkyl groups having from 1 to 6 carbon atoms wherein said carbon atoms may include ether linkages therebetween; and $R_8$ through $R_7$ are independently selected from alkyl groups having from 1 to 10 carbon atoms.

* * * * *

UNITED STATES PATENT AND TRADEMARK OFFICE
CERTIFICATE OF CORRECTION

PATENT NO. : 5,710,302          Page 1 of 2
DATED : Jan. 20, 1998
INVENTOR(S) : Jay F. Kunzler, et al It is certified that error appears in the above-identified patent and that said Letters Patent is hereby corrected as shown below:

In the ABSTRACT, delete

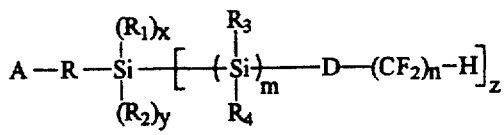

and insert --

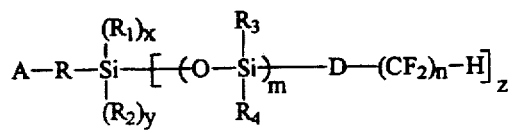

--.

In Column 18, line 13, delete

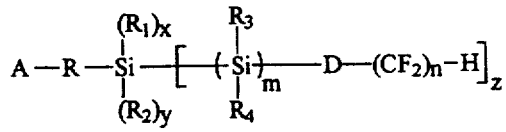

and insert --

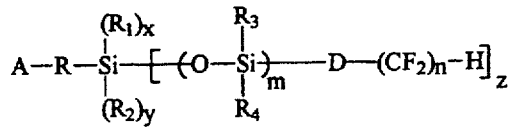

--.

In Column 18, line 17, after "ethylenically", insert -- unsaturated radical -- .

UNITED STATES PATENT AND TRADEMARK OFFICE
CERTIFICATE OF CORRECTION

PATENT NO. : 5,710,302
DATED : Jan. 20, 1998
INVENTOR(S) : Jay F. Kunzler, et al It is certified that error appears in the above-identified patent and that said Letters Patent is hereby corrected as shown below:

In Column 18, line 60, delete

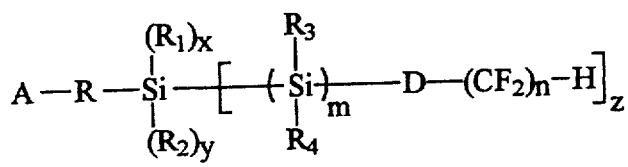

and insert --

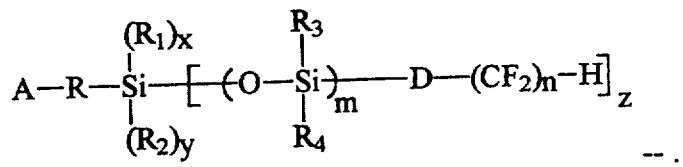

--.

Signed and Sealed this

Twenty-fourth Day of March, 1998

Attest:

BRUCE LEHMAN

Attesting Officer     Commissioner of Patents and Trademarks